US00PP33608P2

(12) United States Plant Patent
Gitzels et al.

(10) Patent No.: US PP33,608 P2
(45) Date of Patent: Nov. 2, 2021

(54) ***DAHLIA* PLANT NAMED 'BALDENASP'**

(50) Latin Name: *Dahlia variabilis*
Varietal Denomination: Baldenasp

(71) Applicant: Ball Horticultural Company, West Chicago, IL (US)

(72) Inventors: Jeroen Gitzels, Zwaag (NL); Valentin Taquet, Amsterdam (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/334,302

(22) Filed: May 28, 2021

Related U.S. Application Data

(60) Provisional application No. 63/139,727, filed on Jan. 20, 2021.

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — Audrey Charles

(57) ABSTRACT

A new and distinct cultivar of *Dahlia* plant named 'Baldenasp', characterized by its double-type, medium red colored inflorescences, dark green-colored foliage, and vigorous, upright-mounded growth habit, is disclosed.

1 Drawing Sheet

Latin name of genus and species of plant claimed: *Dahlia variabilis*.

Variety denomination: 'Baldenasp'.

BACKGROUND OF THE INVENTION

The present invention relates to a new and distinct cultivar of *Dahlia* plant botanically known as *Dahlia variabilis* and hereinafter referred to by the cultivar name 'Baldenasp'.

The new cultivar originated in a controlled breeding program in Hem, The Netherlands during August 2013. The objective of the breeding program was the development of *Dahlia* cultivars that are freely flowering with large inflorescences, mid-season flower timing, and a vigorous, upright-mounded growth habit.

The new *Dahlia* cultivar is the result of open pollination. The female (seed) parent of the new cultivar is the proprietary *Dahlia variabilis* breeding selection coded S-138, not patented, characterized by its semi-double type, dark pink-colored inflorescences, medium green-colored foliage, and moderately vigorous, upright-mounded growth habit. The male (pollen) parent of the new cultivar is unknown. The new cultivar was discovered as a single flowering plant within the progeny of the above stated open pollination during July 2014 in a controlled environment in Hem, The Netherlands.

Asexual reproduction of the new cultivar by terminal stem cuttings since July 2014 in Hem, The Netherlands and Andijk, The Netherlands has demonstrated that the new cultivar reproduces true-to-type with all the characteristics, as herein described, firmly fixed and retained through successive generations of such asexual propagation.

SUMMARY OF THE INVENTION

The following characteristics of the new cultivar have been repeatedly observed and can be used to distinguish 'Baldenasp' as a new and distinct cultivar of *Dahlia* plant:

1. Double-type, medium red colored inflorescences;
2. Dark green-colored foliage; and
3. Vigorous, upright-mounded growth habit.

Plants of the new cultivar differ from plants of the female parent primarily in having medium red colored inflorescences, double-type inflorescences, and increased growth vigor.

Of the many commercially available *Dahlia* cultivars, the most similar in comparison to the new cultivar is DALAYA Vampire 'Baldenrek', U.S. Plant Pat. No. 29,662. However, in comparison, plants of the new cultivar differ from plants of 'Baldenrek' in at least the following characteristics:

1. Plants of the new cultivar have lighter red colored inflorescences than plants of 'Baldenrek';
2. Plants of the new cultivar have larger diameter inflorescences than plants of 'Baldenrek'; and
3. Plants of the new cultivar more ray florets per inflorescence than plants of 'Baldenrek'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldenasp'. The 14-week-old plants were grown in 6.5-inch pots for 10 weeks in a glass-covered greenhouse in Hem, The Netherlands. Plants were given one pinch before transplant.

DETAILED BOTANICAL DESCRIPTION

Figure 1:
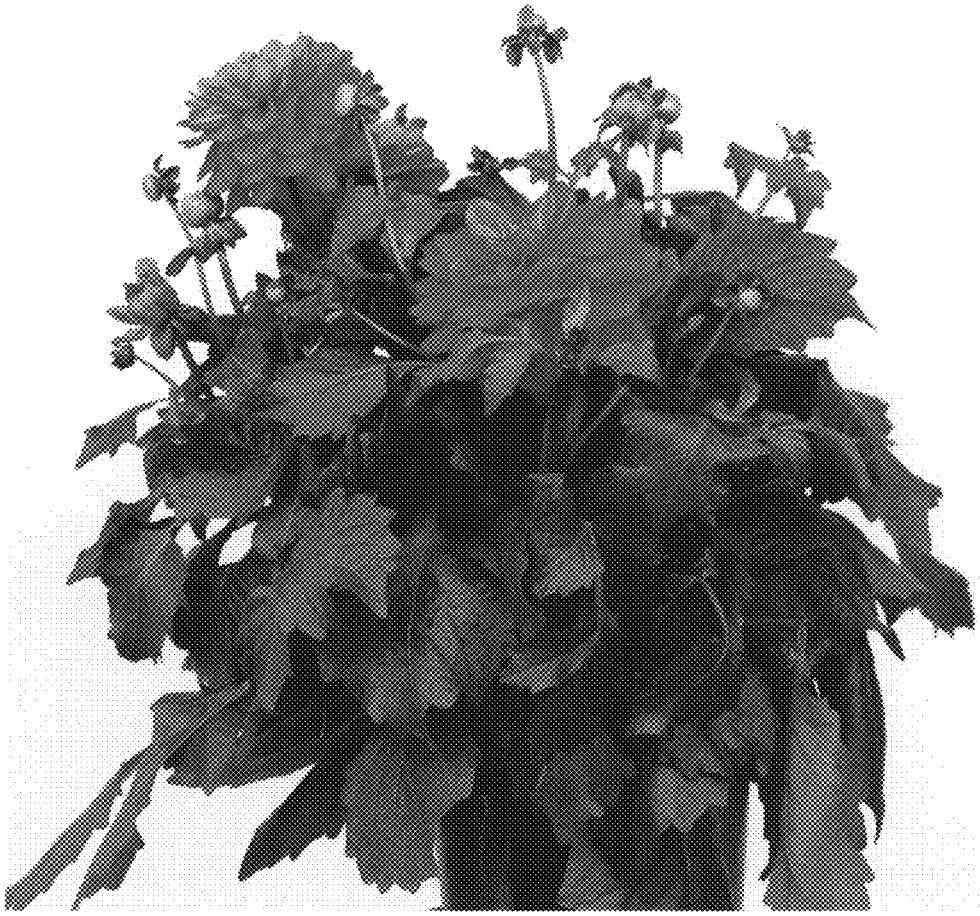
FIG. 1 illustrates a side view of the overall growth and flowering habit of 'Baldenasp'.
Figure 2:
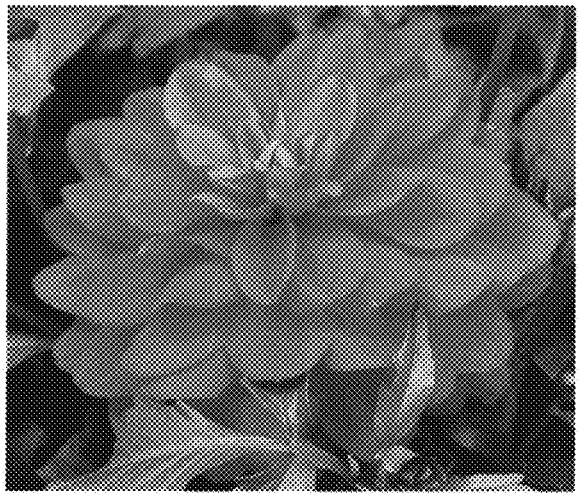
FIG. 2 illustrates a close-up view of an individual inflorescence of 'Baldenasp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The RHS Colour Chart of The Royal Horticultural Society, London, England, 2015 edition, except where general color terms of ordinary significance are used. The color values were determined in March 2021 under natural light conditions in Boskoop, The Netherlands.

The following descriptions and measurements describe 14-week-old plants produced from cuttings from stock plants and grown in a glass-covered greenhouse under conditions comparable to those used in commercial practice. The plants were grown in Hem, The Netherlands in 6.5-inch pots for 10 weeks utilizing a soilless growth medium. Plants were given one pinch before transplant. Three Daminozide treatments were applied: one at 2,500 ppm two weeks after transplant, a second at 3,000 ppm four weeks after transplant and a third at 3,500 ppm six weeks after transplant. Greenhouse temperatures were maintained at an average of approximately 64° F. (18° C.) during the day and approximately 61° F. (16° C.) during the night. Supplemental lighting was used. Measurements and numerical values represent averages of typical plants.

Botanical classification: *Dahlia variabilis* 'Baldenasp'.

Parentage:

*Female parent.*—Proprietary *Dahlia variabilis* breeding selection coded S-138, not patented.

*Male parent.*—Unknown.

Propagation:

*Type cutting.*—Terminal stem.

*Time to initiate roots.*—Approximately 9 to 12 days.

*Time to produce a rooted cutting.*—Approximately 25 to 32 days.

*Root description.*—Fine, fibrous.

*Rooting habit.*—Freely branching.

Plant description:

*Commercial crop time.*—Approximately 7 to 9 weeks from a rooted cutting to finish in a 15 cm pot.

*Growth habit and general appearance.*—Vigorous, upright-mounded.

*Size.*—Height from soil level to top of plant plane: Approximately 29.8 cm. Height from soil level to top of foliage: Approximately 25.0 cm. Width: Approximately 42.2 cm.

*Branch.*—Quantity of lateral branches per plant: Approximately 6. Strength: Moderately strong. Length of lateral branch: Approximately 15.5 cm. Diameter of lateral branch at central internode: Approximately 6.0 mm. Length of central internode of lateral branch: Approximately 3.6 cm. Texture: Glabrous. Color: 146A with 144A, with immature branches tinted with 197A.

Foliage description:

*General description.*—Quantity of leaves per lateral branch: Approximately 10. Type: Simple and compound. Quantity of leaflets per compound leaf: Approximately 3, trifoliate. Fragrance: None detected. Arrangement: Opposite. Aspect: Petiole mostly perpendicular angle to stem with blade extending downward. Shape of leaf and leaflet: Broadly ovate. Margin of leaf and leaflet: Widely serrate. Apex of leaf and leaflet: Acute. Base of leaf and leaflet: Broadly attenuate. Venation pattern: Pinnate.

*Simple leaf.*—Length: Approximately 15.7 cm. Width: Approximately 10.8 cm. Texture of upper and lower surfaces: Sparsely pubescent on venation. Color of upper surface: 139A blended with 147A. Color of lower surface: 191A. Length of petiole: Approximately 5.9 cm. Diameter of petiole: Approximately 4.0 mm. Texture of upper and lower surfaces of petiole: Glabrous. Color of upper surface of petiole: 146C with 146A. Color of lower surface of petiole: 146C.

*Mature trifoliate leaf.*—Shape: Ovate in outline. Length of mature trifoliate leaf: Approximately 17.1 cm. Width of mature trifoliate leaf: Approximately 17.1 cm. Length of terminal leaflet: Approximately 11.4 cm. Width of terminal leaflet: Approximately 8.6 cm. Length of lateral leaflet: Approximately 9.3 cm. Width of lateral leaflet: Approximately 6.0 cm. Texture of upper and lower surfaces: Sparsely pubescent on venation. Color of upper surface: 139A blended with 147A, tinted with 178A at rachis attachment. Color of lower surface: 191A. Length of petiole of mature trifoliate leaf: Approximately 5.4 cm. Diameter of petiole of mature trifoliate leaf: Approximately 4.0 mm. Texture of upper and lower surfaces of petiole: Glabrous. Color of upper surface of petiole: 146C with 146A. Color of lower surface of petiole: 146C. Length of rachis: Approximately 3.6 cm. Diameter of rachis: Approximately 2.0 mm. Texture of upper and lower surfaces of rachis: Glabrous. Color of upper and lower surfaces of rachis: 146C.

Flowering description:

*Flowering habit.*—'Baldenasp' is freely flowering under outdoor growing conditions with substantially continuous blooming from summer through autumn.

*Lastingness of individual inflorescence on the plant.*—Approximately 2 weeks.

Inflorescence description:

*General description.*—Type: Double, composite, consisting of multiple rows or ray florets, and disc florets, persistent. Aspect: Facing upward and outward. Arrangement: Terminal, arising from leaf axils on strong peduncles positioned over the foliage. Disc and ray florets arranged acropetally on a capitulum. Quantity per plant: Approximately 3. Fragrance: None. Shape: Hemispherical to near spherical when ray florets are fully open. Inflorescence diameter: Approximately 10.2 cm. Inflorescence depth: Approximately 6.8 cm. Disc diameter: Approximately 1.0 cm. Receptacle diameter at base: Approximately 1.0 cm. Receptacle depth: Approximately 5.0 mm. Receptacle color: 146D.

*Peduncle.*—Strength: Strong. Aspect: Erect. Length: Approximately 10.7 cm. Diameter: Approximately 4.0 mm. Texture: Glabrous. Color: 146A to 146B tinted with 200B and N200A.

*Bud.*—Rate of bud opening: Generally takes 2 weeks for bud to progress from first color to fully open flower. Quantity per plant: Approximately 35.

*Bud just before opening.*—Shape: Oblate. Depth at first color: Approximately 1.2 cm. Diameter at first color: Approximately 1.3 cm. Texture: Glabrous. Color: Outer surface of the phyllaries 153A with base of 143C.

*Ray florets.*—Quantity per inflorescence: Approximately 100. Arrangement: Imbricate, in multiple whorls. Aspect: Slightly concave. Shape: Obovate. Margin: Entire. Apex: Apiculate. Base: Attenuate. Appearance: Matte. Length: Approximately 4.7 cm. Width: Approximately 2.3 cm. Texture of upper surface: Glabrous. Texture of lower surface: Sparsely pubescent on venation, ribbed. Color of upper surface when first and fully open: 53C. Color of lower surface when first and fully open: 51A with a heavy overlay of 64C at apex and base of 153D. Color of upper surface before senescence: 42A transitioning to 70B at apex. Color of lower surface before senescence: 39B with a heavy overlay of 59C and 60B at apex, venation of 151A.

*Disc florets.*—Quantity per inflorescence: Approximately 20. Arrangement: Massed in center of inflorescence. Aspect: Erect. Shape: Tubular. Margin: Entire. Apex: 5 acute tips. Base: Fused. Length: Approximately 1.4 cm. Diameter at apex: Approximately 2.0 mm. Diameter at base: Approximately 1.0 mm. Texture: Glabrous. Color when fully open: 17A with midsection and base of 145C, translucent.

*Outer phyllaries.*—Quantity: Approximately 5. Aspect: Flat, reflexed. Shape: Narrowly elliptic. Margin: Entire, undulate. Apex: Acute. Base: Truncate. Length: Approximately 1.8 cm. Width: Approximately 1.0 cm. Texture of upper and lower surfaces: Glabrous. Color of upper surface: NN137A to NN137B. Color of lower surface: 147B.

*Inner phyllaries.*—Quantity: Approximately 1 per floret. Shape: Linear, imbricate. Margin: Entire. Apex: Broadly acute to obtuse. Base: Truncate. Length of outermost: Approximately 2.0 cm. Width of outermost: Approximately 7.0 mm. Length of innermost: Approximately 1.3 cm. Width of innermost: Approximately 5.0 mm. Texture of upper and lower surfaces: Glabrous. Color of upper and lower surfaces: 151C, translucent with 143A at base of outermost.

*Reproductive organs.*—Androecium: On disc florets. Stamen quantity: 5 per floret. Stamen length: Approximately 8.0 mm. Anther shape: Linear. Anther length: Approximately 4.0 mm. Anther color: 154C. Pollen amount: Sparse. Pollen color: 23A. Gynoecium: On disc and ray florets. Pistil length: Approximately 9.0 mm. Stigma shape: 2 branched. Stigma length: Approximately 2.0 mm. Stigma width: Approximately 2.0 mm. Stigma color: 14B. Style length: Approximately 7.0 mm. Style color: 154B. Ovary length: Approximately 2.0 mm. Ovary color: 145D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldenasp', substantially as herein illustrated and described.

* * * * *